(12) United States Patent
Liu et al.

(10) Patent No.: US 8,173,637 B2
(45) Date of Patent: *May 8, 2012

(54) STABILIZED ATYPICAL ANTIPSYCHOTIC FORMULATION

(75) Inventors: Fang-yu Liu, Union City, CA (US); Zhi-qun Shen, Hangzhou (CN)

(73) Assignee: Handa Pharmaceuticals, LLC, Fremont, CA (US)

( * ) Notice: Subject to any disclaimer, the term of this patent is extended or adjusted under 35 U.S.C. 154(b) by 717 days.

This patent is subject to a terminal disclaimer.

(21) Appl. No.: 12/205,356

(22) Filed: Sep. 5, 2008

(65) Prior Publication Data

US 2010/0022511 A1    Jan. 28, 2010

Related U.S. Application Data

(60) Provisional application No. 61/083,270, filed on Jul. 24, 2008.

(51) Int. Cl.
- *A01N 43/00* (2006.01)
- *A61K 31/553* (2006.01)
- *A61K 31/554* (2006.01)
- *A61K 9/14* (2006.01)

(52) U.S. Cl. ......... 514/211.13; 514/259.41; 514/254.04; 514/253.06; 514/317; 514/321; 514/323; 514/431; 514/428; 514/220; 514/410; 424/484; 424/489

(58) Field of Classification Search .................. None
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,034,758 A | 7/1977 | Theeuwes | |
| 4,036,228 A | 7/1977 | Theeuwes | |
| 4,077,407 A | 3/1978 | Theeuwes et al. | |
| 4,612,008 A | 9/1986 | Wong et al. | |
| 4,783,337 A | 11/1988 | Wong et al. | |
| 4,786,505 A | 11/1988 | Lovgren et al. | |
| 4,873,337 A | 10/1989 | Sih et al. | |
| 4,879,288 A | 11/1989 | Warawa et al. | |
| 4,984,240 A | 1/1991 | Keren-Zvi et al. | |
| 5,002,776 A | 3/1991 | Geoghegan et al. | |
| 5,071,607 A | 12/1991 | Ayer et al. | |
| 5,229,382 A | 7/1993 | Chakrabarti et al. | |
| 5,314,697 A | 5/1994 | Kwan et al. | |
| 5,529,791 A | 6/1996 | Deboeck et al. | |
| 5,563,134 A | 10/1996 | Fischer et al. | |
| 5,627,178 A | 5/1997 | Chakrabarti et al. | |
| 5,654,005 A | 8/1997 | Chen et al. | |
| 5,948,437 A | 9/1999 | Parikh et al. | |
| 6,099,859 A | 8/2000 | Cheng et al. | |
| 6,251,895 B1 | 6/2001 | Larsen et al. | |
| 6,923,984 B1 | 8/2005 | Remon | |
| 7,959,948 B2 * | 6/2011 | Jansen | 424/486 |
| 2004/0180088 A1 | 9/2004 | Dudhara et al. | |
| 2005/0158383 A1 * | 7/2005 | Boehm et al. | 424/468 |
| 2007/0196491 A1 * | 8/2007 | Venkatesh | 424/480 |
| 2007/0244093 A1 | 10/2007 | Boehm et al. | |
| 2008/0081069 A1 | 4/2008 | Prasad et al. | |
| 2008/0221079 A1 | 9/2008 | Jansen | |
| 2008/0287418 A1 | 11/2008 | Brown et al. | |
| 2009/0004281 A1 | 1/2009 | Nghiem et al. | |
| 2009/0317473 A1 | 12/2009 | Naringrekar et al. | |

FOREIGN PATENT DOCUMENTS

| | | |
|---|---|---|
| WO | 2005041935 | 5/2005 |
| WO | 2006088305 | 8/2006 |
| WO | 2007090091 | 8/2007 |
| WO | 2008060228 | 5/2008 |
| WO | 2010011232 | 1/2010 |

OTHER PUBLICATIONS

A. Wittman-Regis, International Preliminary Report on Patentability in PCT/US08/75333, 4 pages, Jan. 25, 2011, Int'l Bureau of WIPO, Geneva, Switzerland.
Package Insert for SEROQUEL XR, 29 pages, AstraZeneca Pharmaceuticals, Wilmington, DE, May 2007.
U.S. Appl. No. 13/073,873, filed Mar. 28, 2011.
Young; International Search Report in PCT/US08/75333; USPTO; Alexandria, VA; 2 pgs.; Nov. 19, 2008.
Young; Written Opinion of the International Searching Authority in PCT/US08/75333; USPTO; Alexandria, VA; 3 pgs.; Nov. 19, 2008.
61st ed. of Physician's Desk Reference; entry for Risperdal; pp. 1676-1688; Thomson PDR; Montvale, NJ; 2007.
61st ed. of Physician's Desk Reference; entry for Abilify; pp. 2450-2455; Thomson PDR; Montvale, NJ; 2007.
61st ed. of Physician's Desk Reference; entry for Geodon; pp. 2529-2535; Thomson PDR; Montvale, NJ; 2007.

\* cited by examiner

*Primary Examiner* — Robert A Wax
*Assistant Examiner* — William Craigo
(74) *Attorney, Agent, or Firm* — Florek & Endres PLLC

(57) ABSTRACT

A pharmaceutical composition that contains an atypical antipsychotic drug and succinic acid, fumaric acid or a mixture of succinic acid and fumaric acid.

20 Claims, No Drawings

STABILIZED ATYPICAL ANTIPSYCHOTIC FORMULATION

CROSS REFERENCE TO RELATED APPLICATION

This application claims the benefit of U.S. Provisional Patent Application Ser. No. 61/083,270 filed on Jul. 24, 2008.

TECHNICAL FIELD OF THE INVENTION

The present invention relates to a stabilized pharmaceutical composition comprising an atypical antipsychotic drug and at least one organic acid selected from the group consisting of succinic acid, fumaric acid, or mixtures thereof. In particular, the present invention relates to a pharmaceutical composition that contains a diazepine, an oxazepine or a thiazepine atypical antipsychotic drug and at least one organic acid selected from the group consisting of succinic acid, fumaric acid or mixtures thereof. The composition should exhibit a pH of less than 5, preferably less than 4 when the composition is placed in sufficient water to create a 1% weight by volume solution or suspension at approximately 25° C.

BACKGROUND OF THE INVENTION

Atypical antipsychotic drugs are a class of drugs used to treat psychiatric conditions such as schizophrenia, acute mania and bipolar disorders. Some of the early or typical antipsychotic drugs exhibited a number of undesirable side effects such as acute dyskinesias, acute dystonias, motor restlessness, pseudo-Parkinsonism and tardivedyskinesias. These adverse side effects have been referred to as extrapyramidal symptoms.

In an effort to overcome these extrapyramidal symptoms, a group of compounds were developed that are commonly referred to as atypical antipsychotic drugs. These atypical antipsychotic drugs are generally heterocyclic compounds that affect the serotonin and dopamine receptors. Examples of some atypical antipsychotic drugs include clozapine, olanzapine, risperidone, quetiapine, ziprasidone, paliperidone, aripiprazole, asenapine, iloperidone, sertindole, zotepine, amisulpride bifeprunox, melperone and pharmaceutically acceptable salts thereof.

Pharmaceutical dosage forms containing atypical antipsychotic drugs have been described in the literature. For example, the 61$^{st}$ edition of the Physicians' Desk Reference, © 2007 ("PDR"), describes commercially available RISPERDAL® products which are oral solutions, tablets, orally disintegrating tablets and microsphere-containing injections that contain risperidone (see PDR at pages 1676-1688); ABILIFY® products which are oral solutions, tablets and orally disintegrating tablets that contain aripiprazole (see PDR at pages 2450-2455) and GEODON® capsules and injections. Some of these formulations employ organic acids such as citric, tartaric and benzoic acids.

U.S. Pat. No. 5,563,134 discloses clozapine dosage forms that contain an acid scavenger such as ascorbic acid. The ascorbic acid is reported to reduce the occurrences of granulocytopenia or agranulocytosis that is known to occur with the administration of clozapine. U.S. Pat. No. 6,251,895 discloses olanzapine dosage forms that contain benzoic acid. Olanzapine is also commercially available under the tradename ZYPREXA® in an intramuscular formulation that employs tartaric acid.

U.S. Pat. No. 5,948,437 discloses a number of quetiapine dosage forms and indicates organic acids or alkali metals salts of the organic acids may be used as pH modifiers in the dosage forms. Although a number of organic acids are disclosed in this patent, it is reported that the alkali metal salts such as sodium citrate are preferred.

Although many pharmaceutical dosage forms containing atypical antipsychotic drugs have been described in the art, it is an object of the present invention to provide a pharmaceutical composition comprising an atypical antipsychotic drug and an organic acid selected from the group consisting of succinic acid, fumaric acid or mixtures thereof. It is believed that the use of these non-metal, dual carboxyl group organic acids improve the stability of the atypical antipsychotic drug.

It is another object of the present invention to provide a pharmaceutical dosage form comprising an atypical antipsychotic drug and an organic acid selected from the group consisting of succinic acid, fumaric acid or mixtures thereof that can be administered orally.

It is yet another object of the present invention to provide a controlled release pharmaceutical dosage form comprising an atypical antipsychotic drug and an organic acid selected from the group consisting of succinic acid, fumaric acid or mixtures thereof.

It is still a further object of the present invention to provide a controlled release pharmaceutical dosage form comprising an atypical antipsychotic drug and an organic acid selected from the group consisting of succinic acid, fumaric acid or mixtures thereof that is free of any swelling or hydrogel polymeric materials.

These and other objects of the present invention will become apparent from a review of the appended specification.

SUMMARY OF THE INVENTION

The present invention accomplishes the above objects and others by providing a novel pharmaceutical composition comprising an atypical antipsychotic drug and an organic acid selected from the group consisting of succinic acid, fumaric acid or mixtures thereof. The composition should exhibit a pH of less than 5, preferably less than 4, when a 1% weight by volume aqueous solution or suspension is prepared at 25° C.

In one embodiment of the present invention, the succinic acid, fumaric acid or mixture thereof should comprise at least about 5 weight percent of the composition, preferably at least about 10 weight percent of the composition and most preferably at least about 20 weight percent of the composition.

The composition may be an intermediate composition or a final formulation or dosage form. The composition should also comprise at least one additional pharmaceutical excipient.

One embodiment of the present invention is a solid composition.

In an alternate embodiment of the present invention, the composition is a controlled release formulation that comprises an atypical antipsychotic drug, an organic acid selected from the group consisting of succinic acid, fumaric acid or mixtures thereof and a rate controlling excipient. The rate controlling excipient can be a film forming polymer that forms a coating or barrier around the formulation or a matrix forming material. A further embodiment of the controlled release formulation comprises an atypical antipsychotic drug, an organic acid selected from the group consisting of succinic acid, fumaric acid or mixtures thereof and a hydrophobic matrix material, i.e., a non-swelling and/or non-gelling matrix material.

DETAILED DESCRIPTION OF THE INVENTION

The subject invention concerns a stable pharmaceutical composition comprising an atypical antipsychotic drug and an organic acid selected from the group consisting of succinic acid, fumaric acid or mixtures thereof. Examples of atypical antipsychotic drugs that may be used in the present invention include clozapine, olanzapine, risperidone, quetiapine, ziprasidone, paliperidone, aripiprazole, asenapine, iloperidone, sertindole, zotepine, amisulpride bifeprunox, melperone and pharmaceutically acceptable salts, isomers and metabolites of the aforementioned drugs. A more complete list of atypical antipsychotic drugs can be found in *Remington: The Science and Practice of Pharmacy*, 20$^{th}$ edition and in the United States Pharmacopeia 29, both of which are incorporated herein by reference.

A preferred group of the atypical antipsychotic drugs useful in the present invention include the diazepines, oxazepines and thiazepines and pharmaceutically acceptable salts thereof. The more preferred group of atypical antipsychotic drugs useful in the present invention are olanzapine and quetiapine as described in U.S. Pat. Nos. 5,229,382; 5,627,178; 6,251,895 and 4,879,288, which are incorporated herein by reference. The most preferred atypical antipsychotic drugs are pharmaceutically acceptable salts of quetiapine such as the fumarate and hydrochloride salts.

The amount of antipsychotic drug employed in the dosage forms prepared in accordance with the present invention can range from 0.25 mg to 500 mg. The amount in the final dosage forms will vary depending upon the atypical antipsychotic drug selected and the dosage form containing the drug. It is within the ordinary skill in the art to determine the appropriate amount of atypical antipsychotic drug based upon the reported therapeutic amounts for the known antypical antipsychotic drugs.

The present invention will also comprise an organic acid selected from the group consisting of succinic acid, fumaric acid and mixtures thereof. Succinic acid is also known as amber acid, ethylenesuccinic acid, and 1,4-butanedioic acid. Succinic acid can be prepared by hydrogenation of maleic or fumaric acid or by aqueous alkali or acid hydrolysis of succinonitrile. It is reported in the Merck Index that 1 gram of succinic acid can dissolve in 13 ml of cold water and 1 ml of boiling water. The United States Food and Drug Administration (FDA) has identified succinic acid as a GRAS compound (generally recognized as safe) when used as a food additive in small amounts. For example, 21 C.F.R. §184.1091 identifies succinic acid as a flavor enhancer and a pH control agent.

Fumaric acid is also known as (E)-butenedioic acid, trans-1,2-ethylenedicarboxylic acid, 2-butenedioic acid, allomaleic acid, boletic acid, lichenic acid and trans-butenedioic acid. The Merck Index indicates that 0.63 grams of fumaric acid are soluble in 100 grams of water at 25° C. Fumaric acid has been used as a flavor enhancing agent and a pH modifying agent.

Compositions in accordance with the present invention should exhibit a pH of less than 5, preferably less than 4 when a 1% weight by volume aqueous solution or suspension is prepared and measured at 25° C. In one embodiment of the present invention, the composition should exhibit a pH between 2 and 5, preferably between 2.5 and 4.5 and most preferably between 3 and 4 when a 1% weight by volume aqueous solution or suspension of the composition is prepared and measured at 25° C.

Embodiments of the present invention may comprise about 5 to about 95 weight percent, preferably about 10 to about 90 weight percent of the composition and most preferably about 15 to about 85 weight percent of the composition of the succinic acid, fumaric acid or mixture of succinic and fumaric acid.

In certain embodiments of the present invention, such as solid oral dosage forms, the solid oral dosage form should exhibit a pH between 2 and 5, preferably between 2.5 and 4.5 and most preferably between 3 and 4 when a 1% weight by volume aqueous solution or suspension of the dosage form ingredients is prepared and measured at 25° C. comprises. These solid oral dosage forms typical comprise at least about 5 weight percent of the organic acid selected from succinic acid, fumaric acid or mixtures thereof, preferably at least about 10 weight percent and most preferably at least about 15 weight percent. In certain controlled release dosage forms prepared in accordance with the present invention, it has been discovered that the succinic acid, fumaric acid or mixture of succinic acid and fumaric acid should comprise at least 20 weight percent of the total weight of the controlled release dosage form, preferably at least 25 weight percent and most preferably at least 27.5 weight percent.

The ratio of atypical antipsychotic drug to organic acid in the pharmaceutical composition prepared in accordance with the present invention should be about 5:1 to 1:5 and preferably about 3:1 to 1:3 depending upon the atypical antipsychotic drug selected.

The present invention should also include at least one additional pharmaceutically acceptable excipient. The pharmaceutically acceptable excipients useful in the present invention can be selected from the group consisting of fillers, binders, lubricants, glidants, antiadherents, flavoring agents, coloring agents, disintegrants and mixtures of thereof. A more detailed description of the acceptable pharmaceutical excipients that may be employed in the present invention can be found in Rowe et al., *Handbook of Pharmaceutically Acceptable Excipients* (4$^{th}$ ed. 2003) or the United States Pharmacopeia 29, both of which are incorporated herein by reference.

Examples of acceptable fillers, sometimes referred to as diluents, include water; sugars such as lactose, dextrose, sucrose, maltose, or microcrystalline cellulose; clays and mixtures thereof.

Binders that are useful in the present invention include pharmaceutically acceptable substances with cohesive properties. Some examples include celluloses such as hydroxypropyl methylcellulose, hydroxypropyl cellulose and carboxymethycellulose sodium; polyvinylpyrrolidone; sugars; starches and mixtures thereof.

Examples of lubricants, glidants and/or antiadherents that may be used in the present invention include talc, magnesium stearate, calcium stearate, stearic acid, hydrogenated vegetable oils, polyethylene glycols, silicon dioxide and mixtures thereof.

Flavoring agents that can be used in the present invention include peppermint, spearmint, wintergreen, cinnamon, coconut, coffee, chocolate, vanilla, menthol, liquirice, anise, apricot, caramel, pineapple, strawberry, raspberry, grape, cherry, mixed berry, tropical fruits, mint and mixtures thereof.

Coloring agents that may be employed in the present invention include FD&C-type dyes and lakes, fruit and vegetable extracts, titanium dioxide and mixtures thereof.

Examples of disintegrating agents that can be used in the present invention include corn starch, croscarmelose sodium, crospovidone (polyplasdone XL-10), sodium starch glycolate (EXPLOTAB or PRIMOJEL) or any combination of the foregoing.

The pharmaceutical composition of the present invention can be any type of composition known in the pharmaceutical arts such as a solution, suspension, emulsion or solid. The composition can be an intermediate used in the manufacture of a dosage form or may be a dosage form designed for parental, intravenous, ophthalmic, oral, buccal, rectal or vaginal delivery. The preferred embodiment of the present invention is a solid oral dosage form such as an orally disintegrating tablet, an immediate release dosage form, a delayed or enteric coated dosage form, a controlled release dosage form or a combination of the forgoing.

An immediate release dosage form in accordance with the present invention may be prepared using techniques commonly known in the art and can be in the form of a tablet or capsule.

In forming an immediate release tablet in accordance with the present invention, an atypical antipsychotic drug, an organic acid selected from the group consisting of succinic acid, fumaric acid or mixtures thereof and at least one additional excipient such as a binder, filler and lubricant are mixed together using standard techniques known in the art such as blending, slugging and/or granulation. The mixture can be compressed into tablets using techniques commonly used in the art. Once the mixture has been compressed and formed into a tablet core, it may optionally be coated with a seal coating or an aesthetic coating. The seal coating or aesthetic coating typically is a coating or layer that is soluble or rapidly disintegrating in water and does not materially affect the release of the active ingredients from the tablet core. The most common seal coatings comprise low molecular weight hydroxypropyl methylcellulose or polyvinyl alcohol. Some typical seal coats are described in U.S. Pat. Nos. 4,786,505; 6,099,859 and 5,314,697, which are incorporated herein by reference.

An immediate release composition in accordance with the present invention may also be prepared by blending an atypical antipsychotic drug, organic acid selected from the group consisting of succinic acid, fumaric acid or mixtures thereof and at least one additional excipient such as a filler and loading the blended mixture into a gelatin capsule.

The following table provides a representative composition that can be prepared in accordance with the present invention:

TABLE 1

| Materials | Preferred | Most Preferred |
|---|---|---|
| Atypical Antipsychotic Drug | 0.5-75% | 1-50% |
| Organic Acid(s) | 5-75% | 20-60% |
| Filler | 5-70% | 10-65% |
| Glidant | 0-5% | 0.1-3% |
| Lubricant | 0-5% | 0.1-3% |

The above percentages are based upon the total weight of the composition. The above composition can be further processed into a dosage form such as a tablet or capsule.

A controlled release dosage form in accordance with the present invention may also be prepared using techniques commonly known in the art. Some of the controlled release dosage forms that are useful in the present invention include, but are not limited, to matrix tablets, osmotic tablets, pellet filled capsules or combinations of the foregoing. Release controlling excipients such as hydrophilic and hydrophobic matrix polymers and polymeric coatings are known in the art and described in Rowe et al., *Handbook of Pharmaceutically Acceptable Excipients* (4th ed. 2003), which is incorporated herein by reference. The controlled release dosage form in accordance with the present invention should release therapeutically effective amounts of the atypical antipsychotic drug over a period of 4-24 hours, preferably 8-24 hours, so the dosage form can be administered once or twice daily.

One embodiment of a controlled release dosage form in accordance with the present invention is a matrix tablet. The matrix tablet should comprise therapeutically effective amount of the atypical antipsychotic agent, a stabilizing amount of an organic acid selected from the group consisting of succinic acid, fumaric acid or mixtures thereof and a matrix forming agent. The matrix forming agent can be a hydrophobic material such as a wax, a hydrophilic material such as a hydrogel polymer or a combination of the two. As used herein, a hydrogel polymer is a polymeric material that gels or swells when placed in an aqueous environment. The matrix forming agent will control the release of the atypical antipsychotic drug by diffusion of the drug from the matrix, erosion of the matrix or a combination of diffusion and erosion. The amount of diffusion and erosion will depend upon the materials selected for the formation of the matrix.

Examples of hydrogel forming polymers include hydroxypropyl methylcellulose, carboxymethylcellulose calcium, carboxymethylcellulose sodium, guar gum, hydroxyethyl cellulose, hydroxypropyl cellulose, methyl cellulose, acrylic polymers and copolymers, sodium alginate, polyethylene oxides and mixtures thereof.

Examples of hydrophobic materials that can be used to form a non-gelling or non-swelling controlled release matrix for the atypical antipsychotic drug include beeswax, white wax, emulsifying wax, hydrogenated vegetable oil, hydrogenated castor oil, microcrystalline wax, cetyl alcohol, stearyl alcohol, free wax acids such as stearic acid, esters of wax acids, propylene glycol monostearate, glycerol monostearate, carnauba wax, palm wax, candelilla wax, lignite wax, ozokerite, ceresin wax, lardaceine, China wax and mixtures thereof. Other possible rate controlling excipients useful in the present invention include saturated hydrocarbons having from 25 to 31 carbon atoms, saturated alcohols having from 25 to 31 carbon atoms, saturated monocarboxylic acids having from 25 to 31 carbon atoms, esters obtained from said alcohols and monocarboxylic acids which are described in U.S. Pat. No. 6,923,984, incorporated herein by reference.

A combination of hydrophobic and hydrophilic materials may also be used in preparing a controlled release matrix of the present invention.

The controlled release matrix in accordance with the present invention may further comprise conventional excipients that improve the processing or modify the release characteristics. Examples of these conventional excipients include fillers, glidants and lubricants described previously.

One embodiment of the controlled release matrix dosage form in accordance with the present invention and without a gelling or swelling polymer should comprise the following composition:

| Ingredient | Preferred % w/w | Most Preferred % w/w |
|---|---|---|
| Atypical Antipsychotic | 25-75 | 35-65 |
| Organic Acid(s) | 15-60 | 20-50 |
| Hydrophobic Rate | | |
| Controlling Excipient | 1-25 | 3-15 |
| Filler | 0.5-25 | 1-15 |
| Lubricant/Glidant | 0-15 | 0.1-10 |

The above-described hydrophobic matrix tablet may also comprise a placebo layer or layers applied to one or more surfaces of the hydrophobic matrix tablet. The placebo layer is designed to reduce the surface area of the hydrophobic matrix tablet when the tablet is exposed to the environment of use. The reduction in surface area contributes to controlling the release of the atypical antipsychotic drug from the hydrophobic matrix. The placebo layer may comprise any of the aforementioned hydrophobic or hydrophilic matrix materials, although the hydrophobic materials are preferred. The placebo layer should cover about 5% to about 75%, preferably about 10% to about 65% and most preferably about 15% to about 50% of the surface area of the hydrophobic matrix tablet.

Once the matrix tablet has been formed, it may optionally be seal coated or coated with an aesthetic coating as described above with respect to the immediate release composition.

An immediate release coating comprising the atypical antipsychotic drug can be coated directly onto the controlled release matrix core or applied over the sealed coated controlled release matrix core. The immediate release coating comprises the atypical antipsychotic drug and a film forming material or binder and, optionally, other conventional additives such as lubricants, fillers and antiadherents.

The immediate release coating may be applied by any conventional technique such as pan coating or spray coating. In the preferred embodiment, the immediate release coating is applied by spraying an aqueous solution or suspension over a pan containing the matrix cores. The film forming material or binder employed in the immediate release coating is preferably a water soluble or rapidly dispersing material such as a low molecular weight hydroxypropyl methylcellulose or povidone.

Another embodiment of the controlled release dosage form in accordance with the present invention is an osmotic tablet. The osmotic tablet may comprise: a core containing a therapeutic amount of the atypical antipsychotic drug and organic acid selected from the group consisting of succinic acid, fumaric acid or mixtures thereof; a semi permeable membrane surrounding the core; and a passageway in the semi permeable membrane for release of the drug.

The core of the osmotic tablet can be prepared with or without a gelling or swelling polymer. The core of the osmotic tablet can be a homogenous blend of atypical antipsychotic drug, organic acid selected from succinic acid, fumaric acid or mixtures thereof and pharmaceutical excipients as described in U.S. Pat. No. 5,654,005 or a multilayered structure comprising a drug composition and a push composition as described in U.S. Pat. No. 4,612,008 or 4,873,337. The aforementioned patents are incorporated herein by reference.

The osmotic core can optionally be seal coated prior to the application of the semipermeable membrane. The semi permeable membrane should be permeable to the passage of an external fluid such as water or aqueous biological fluids and should be impermeable to the passage of the active ingredients in the osmotic core. Materials that are useful in forming the semi permeable membranes are ethylcellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate and cellulose acetate butyrate. Other suitable polymers are described in U.S. Pat. Nos. 3,845,770; 3,916,899; 4,008,719; 4,036,228 and 4,612,008, which are incorporated herein by reference. The most preferred semi permeable membrane material is cellulose acetate comprising an acetyl content of 39.3% to 40.3%, and is commercially available from Eastman Fine Chemicals.

In an alternative embodiment, the semipermeable membrane can include one of the above-described polymers and a flux-enhancing agent. The flux-enhancing agent can increase the volume of fluid imbibed into the core to enable the composition to dispense substantially all of the active ingredients through the passageway and/or the pores created in the membrane by the dissolution of the flux-enhancing agent. The flux-enhancing agent can be a water-soluble material or an enteric material. Examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108, which are commercially available from BASF) and mixtures thereof. A preferred flux enhancer is PEG 400.

The flux-enhancing agent comprises approximately 0% to about 40% of the total weight of the membrane coating, most preferably about 2% to about 20% of the total weight of the membrane coating. The flux-enhancing agent dissolves or leaches from the semipermeable membrane to form paths in the semipermeable membrane which enables fluid to enter the osmotic core and dissolve the atypical antipsychotic drug.

The semipermeable membrane may also be formed using a commonly known excipient such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the *Encyclopedia of Polymer Science and Technology*, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and combinations thereof. Depending on the particular plasticizer, amounts from about 0% to about 25%, and preferably about 2% to about 15%, of the plasticizer can be used based upon the total weight of the membrane coating.

Generally, the membrane coating around the core will comprise from about 1% to about 5%, and preferably about 2% to about 3%, based upon the total weight of the core and coating.

In a preferred embodiment, the membrane coating surrounding the core further comprises a passageway that will allow for controlled release of the drug from the core. As used herein, the term "passageway" includes an aperture, orifice, bore, hole, weakened area or an erodible element such as a gelatin plug that erodes to form an osmotic passageway for the release of the active ingredients from the dosage form. Passageways used in accordance with the subject invention are well known and are described in U.S. Pat. Nos. 3,845,770; 3,916,899; 4,034,758; 4,077,407; 4,783,337 and 5,071,607, which are incorporated herein by reference.

An immediate release coating(s) may be applied to the semipermeable membrane. The immediate release coatings are described above and may be applied by, but would not be limited to, the processes selected from the group consisting of drug layering, lamination or dry compression. In a preferred embodiment, a seal coat is applied to the semi-permeable membrane before the immediate release layer is applied.

Another embodiment of the controlled release dosage form in accordance with the present invention comprises beads, pellets or mini-tablets comprising the active ingredients. The beads, pellets or mini-tablets may be filled into hard or soft gelatin capsules or compressed into a tablet.

The bead, pellets or mini-tablets are prepared by methods commonly known in the art and typically range in size from about 0.1 mm to about 3 mm in diameter. Ideally, the beads or pellets are about 0.2 to about 1 mm in diameter and the mini-tablets are about 0.5 to about 2.5 mm in diameter.

Active or immediate release beads or pellets are prepared by layering a composition in accordance with the present invention onto an inert substrate such as a non-pariel seed or a microcrystalline cellulose seed commercially available under the tradename CELPHERE®. Active beads or pellets can also be prepared by preparing a composition in accordance with the present invention and subjecting the composition to extrusion spheronization techniques. The composition should comprise a mixture of an atypical antipsychotic drug, organic acid selected from the group consisting of succinic acid, fumaric acid or mixtures thereof and at least one additional conventional pharmaceutical excipient such as a binder and/or filler. The mixture of active ingredients and conventional pharmaceutical excipients can also be compressed in mini-tablets. The active or immediate release beads or pellets can be also prepared by the methods described in U.S. Pat. Nos. 5,529,791 and 4,984,240, which are incorporated herein by reference.

Once the active or immediate release beads, pellets or mini-tablets are prepared, they may be coated with a release controlling polymer coating. The controlled release coating should comprise a water insoluble, water permeable polymer and, optionally, a water or acid soluble channeling agent. The controlled release coating may also comprise a lubricating or dusting agent and, optionally, a surfactant.

Suitable water insoluble, water permeable polymers are ethylcellulose, cellulose acetate and polyacrylates or mixtures thereof. Additional water insoluble polymers are described in U.S. Pat. No. 5,002,776 which is incorporated herein by reference.

One embodiment of the controlled release bead, pellet or mini-tablet dosage form of the present invention employs a water insoluble, water permeable polymer coating such as a polymethacrylate ester copolymer, preferably a poly(ethylacrylate methylmethacrylate) copolymer which is commercially available from Rohm Pharma under the tradename EUDRAGIT NE 30D.

The channeling agent employed in the bead, pellet or mini-tablet coating can be any type of water or acid soluble pharmaceutically acceptable substance commonly known in the art such as polyvinyl pyrrolidone, hydroxyethylcellulose, hydroxypropyl cellulose, hydroxypropyl methylcellulose, sucrose or any combination of the foregoing. The preferred channeling agent is a water or acid soluble polymer such as a low viscosity hydroxypropyl methylcellulose.

Suitable surfactants that may optionally be used in the controlled release coating for the beads, pellets or mini-tablets are sodium lauryl sulfate, sodium taurocholate or a polysorbate.

The controlled release coating can be applied to the active beads, pellets or mini-tablets by any means commonly known in the industry such as a rotary granulator, pan coater or a fluidized bed coater.

Once the bead, pellets or mini-tablets are coated they may be dusted with a suitable lubricant such as talc, magnesium stearate, silicon dioxide, kaolin or a mixture of the foregoing. The lubricant will prevent the beads, pellets or mini-tablets from sticking to one another during processing.

In one embodiment of the present invention, the active or immediate release beads, pellets or mini-tablets comprising the atypical antipsychotic drug and organic acid selected from the group consisting of succinic acid, fumaric acid or mixtures thereof are prepared. A portion of the active or immediate release beads, pellets or mini-tablets are then subsequently coated with a controlled release coating. Various blends of the active and controlled release coated beads, pellets or mini-tablets are blended and filled into hard gelatin capsules. For example, a blend of 20% active beads and 80% controlled release beads are filled into a hard gelatin capsule to prepare a once-a-day capsule dosage form in accordance with the present invention.

A delayed release dosage form in accordance with the present invention may also be prepared by first preparing an immediate release tablet core, a controlled release matrix core or active bead, pellet or mini-tablet core as described above. The cores are then coated with an enteric or pH sensitive coating using techniques commonly known in the art.

The enteric or pH dependent coating material useful in preparing a delayed release coating include zein, shellac, methacrylic acid copolymers, cellulose acetate phthalate, hydroxypropyl methylcellulose phthalate, hydroxypropyl methylcellulose acetate succinate, cellulose acetate trimellitate, polyvinyl acetate phthalate or mixtures thereof.

The delayed release coating should be applied so that the atypical antipsychotic drug present in the core is released only after the composition has passed through the stomach. To insure that the atypical antipsychotic drug present in the core is not released until the composition has left the stomach, the delayed release coating should be designed to dissolve at a pH greater than 4.5, preferably greater than 5.5 and most preferably greater than a pH of 6.

The delayed release coating may also comprise plasticizers and other conventional processing aids as described above.

The delayed release dosage form in accordance with the present invention may also comprise an immediate release component. For example, in the case of a delayed release tablet, the enteric or pH dependent coated tablet may be coated with an immediate release layer as described previously. In the case of enteric coated pellets, a blend of enteric coated pellets and immediate release pellets can be blended together and filled into a hard gelatin capsule or compressed into a tablet. The combination of enteric or pH coated compositions and immediate release component will allow the pulsatile delivery of the atypical antipsychotic drug from a single dosage form.

The pharmaceutical compositions and dosage forms prepared in accordance with the present invention should contain less than 0.5 weight percent of total active ingredient impurities based upon the total weight of the composition or dosage form, preferably less than 0.3 weight percent and most preferably less than 0.25 weight percent of total active impurities when the composition or dosage form is placed in an open container and exposed to 60% relative humidity and 60° C. for two weeks.

DESCRIPTION OF THE PREFERRED EMBODIMENTS

The following are provided by way of example only and are by no means intended to be limiting.

Example 1

A composition in accordance with the present invention was prepared by mixing equal amounts of quetiapine fumarate and succinic acid, i.e., 1:1 ratio. The composition was placed in an open container and subjected to accelerated stability conditions of 60° C. and 60% humidity for two weeks. The impurity profile of the composition was determined by HPLC as follows:

% Unknown Impurity with RRT* 0.47

| Time point | Sample 1 | Sample 2 | Average |
|---|---|---|---|
| initial | 0.0332 | 0.0336 | 0.0334 |
| 1 week | 0.0301 | 0.0312 | 0.0307 |
| 2 weeks | 0.0350 | 0.0382 | 0.0366 |

*RRT = relative retention time

% Unknown Impurity with RRT* 0.59

| Time point | Sample 1 | Sample 2 | Average |
|---|---|---|---|
| initial | Below Detectable limits | Below Detectable limits | Below Detectable limits |
| 1 week | 0.0183 | 0.0179 | 0.0181 |
| 2 weeks | 0.0300 | 0.0312 | 0.0306 |

*RRT = relative retention time

% Unknown Impurity with RRT* 0.89

| Time point | Sample 1 | Sample 2 | Average |
|---|---|---|---|
| initial | 0.0682 | 0.0695 | 0.0689 |
| 1 week | 0.0721 | 0.0716 | 0.0719 |
| 2 weeks | 0.0807 | 0.0798 | 0.0803 |

*RRT = relative retention time

% Total Unknown Impurities

| Time point | Sample 1 | Sample 2 | Average |
|---|---|---|---|
| initial | 0.102 | 0.104 | 0.103 |
| 1 week | 0.120 | 0.120 | 0.120 |
| 2 weeks | 0.146 | 0.149 | 0.148 |

Example 2

A composition in accordance with the present invention was prepared by mixing equal amounts of quetiapine fumarate and fumaric acid, i.e., 1:1 ratio. The composition was placed in an open container and subjected to accelerated stability conditions of 60° C. and 60% humidity for two weeks. The impurity profile of the composition was determined by HPLC as follows:

% Unknown Impurity with RRT* 0.33

| Time point | Sample 1 | Sample 2 | Average |
|---|---|---|---|
| initial | 0.0158 | 0.0167 | 0.0163 |
| 1 week | 0.0119 | 0.0127 | 0.0123 |
| 2 weeks | 0.0137 | 0.0157 | 0.0147 |

*RRT = relative retention time

% Unknown Impurity with RRT* 0.47

| Time point | Sample 1 | Sample 2 | Average |
|---|---|---|---|
| Initial | 0.0322 | 0.0328 | 0.0325 |
| 1 week | 0.0309 | 0.0309 | 0.0309 |
| 2 weeks | 0.0330 | 0.0337 | 0.0334 |

*RRT = relative retention time

% Unknown Impurity with RRT* 0.89

| Time point | Sample 1 | Sample 2 | Average |
|---|---|---|---|
| initial | 0.0708 | 0.0698 | 0.0703 |
| 1 week | 0.0698 | 0.0697 | 0.0698 |
| 2 weeks | 0.0726 | 0.0721 | 0.0724 |

*RRT = relative retention time

% Total Unknown Impurities

| Time point | Sample 1 | Sample 2 | Average |
|---|---|---|---|
| initial | 0.119 | 0.119 | 0.119 |
| 1 week | 0.113 | 0.114 | 0.114 |
| 2 weeks | 0.119 | 0.121 | 0.120 |

Comparative Example 1

A composition not in accordance with the present invention was prepared by mixing equal amounts of quetiapine fumarate and citric acid monohydrate, i.e., 1:1 ratio. The composition was placed in an open container and subjected to accelerated stability conditions of 60° C. and 60% humidity for two weeks. The impurity profile of the composition was determined by HPLC as follows:

% Unknown Impurity with RRT* 0.33

| Time point | Sample 1 | Sample 2 | Average |
|---|---|---|---|
| initial | 0.0100 | 0.0097 | 0.0099 |
| 1 week | 17.3115 | 20.668 | 18.9898 |
| 2 weeks | 17.4295 | 19.3841 | 18.4068 |

*RRT = relative retention time

% Unknown Impurity with RRT* 0.36

| Time point | Sample 1 | Sample 2 | Average |
|---|---|---|---|
| Initial | Below Detectable limits | Below Detectable limits | Below Detectable limits |
| 1 week | 8.2142 | 10.794 | 9.5041 |
| 2 weeks | 14.1043 | 18.4762 | 16.2903 |

*RRT = relative retention time

| % Unknown Impurity with RRT* 0.47 | | | |
|---|---|---|---|
| Time point | Sample 1 | Sample 2 | Average |
| initial | 0.0323 | 0.0324 | 0.0324 |
| 1 week | 0.0136 | 0.0136 | 0.0136 |
| 2 weeks | 0.0161 | 0.0502 | 0.0332 |

*RRT = relative retention time

| % Unknown Impurity with RRT* 0.53 | | | |
|---|---|---|---|
| Time point | Sample 1 | Sample 2 | Average |
| initial | — | — | — |
| 1 week | 0.0340 | 0.0757 | 0.0549 |
| 2 weeks | 0.0837 | 0.2570 | 0.1704 |

*RRT = relative retention time

| % Unknown Impurity with RRT* 0.59 | | | |
|---|---|---|---|
| Time point | Sample 1 | Sample 2 | Average |
| Initial | — | — | — |
| 1 week | 0.2615 | 0.3827 | 0.3221 |
| 2 weeks | 0.3943 | 0.7645 | 0.5794 |

*RRT = relative retention time

| % Unknown Impurity with RRT* 0.89 | | | |
|---|---|---|---|
| Time point | Sample 1 | Sample 2 | Average |
| initial | 0.0702 | 0.0692 | 0.0697 |
| 1 week | 0.0566 | 0.0538 | 0.0552 |
| 2 weeks | 0.0533 | 0.0585 | 0.0559 |

*RRT = relative retention time

| % Total Unknown Impurities | | | |
|---|---|---|---|
| Time point | Sample 1 | Sample 2 | Average |
| initial | 0.112 | 0.112 | 0.112 |
| 1 week | 25.891 | 31.987 | 28.939 |
| 2 weeks | 32.081 | 38.990 | 35.5355 |

Comparative Example 2

A composition not in accordance with the present invention was prepared by mixing equal amounts of quetiapine fumarate and monosodium dihydrogen citrate, i.e., 1:1 ratio. The composition was placed in an open container and subjected to accelerated stability conditions of 60° C. and 60% humidity for two weeks. The impurity profile of the composition was determined by HPLC as follows:

| % Unknown Impurity with RRT* 0.47 | | | |
|---|---|---|---|
| Time point | Sample 1 | Sample 2 | Average |
| initial | 0.0357 | 0.0327 | 0.0342 |
| 1 week | 0.0295 | 0.0318 | 0.0307 |
| 2 weeks | 0.0351 | 0.0361 | 0.0356 |

*RRT = relative retention time

| % Unknown Impurity with RRT* 0.89 | | | |
|---|---|---|---|
| Time point | Sample 1 | Sample 2 | Average |
| initial | 0.0700 | 0.0688 | 0.0694 |
| 1 week | 0.0699 | 0.0687 | 0.0693 |
| 2 weeks | 0.0725 | 0.0739 | 0.0732 |

*RRT = relative retention time

| % Total Unknown Impurities | | | |
|---|---|---|---|
| Time point | Sample 1 | Sample 2 | Average |
| initial | 0.106 | 0.101 | 0.104 |
| 1 week | 0.100 | 0.100 | 0.100 |
| 2 weeks | 0.108 | 0.110 | 0.109 |

Comparative Example 3

A composition not in accordance with the present invention was prepared by mixing equal amounts of quetiapine fumarate and tartaric acid, i.e., 1:1 ratio. The composition was placed in an open container and subjected to accelerated stability conditions of 60° C. and 60% humidity for two weeks. The impurity profile of the composition was determined by HPLC as follows:

| % Unknown Impurity with RRT* 0.33 | | | |
|---|---|---|---|
| Time point | Sample 1 | Sample 2 | Average |
| initial | 0.0137 | 0.0146 | 0.0142 |
| 1 week | 0.0363 | 0.0374 | 0.0369 |
| 2 weeks | 0.1813 | 0.1947 | 0.1880 |

*RRT = relative retention time

| % Unknown Impurity with RRT* 0.50 | | | |
|---|---|---|---|
| Time point | Sample 1 | Sample 2 | Average |
| Initial | 0.0345 | 0.0341 | 0.0343 |
| 1 week | 0.9724 | 1.0025 | 0.9875 |
| 2 weeks | 2.9422 | 3.1656 | 3.0539 |

*RRT = relative retention time

| % Unknown Impurity with RRT* 0.59 | | | |
|---|---|---|---|
| Time point | Sample 1 | Sample 2 | Average |
| initial | — | — | — |
| 1 week | 0.0422 | 0.0424 | 0.0423 |
| 2 weeks | 0.1856 | 0.1953 | 0.1905 |

*RRT = relative retention time

| % Unknown Impurity with RRT* 0.89 | | | |
|---|---|---|---|
| Time point | Sample 1 | Sample 2 | Average |
| initial | 0.0700 | 0.0705 | 0.0703 |
| 1 week | 0.0688 | 0.0696 | 0.0692 |
| 2 weeks | 0.0701 | 0.0705 | 0.0703 |

*RRT = relative retention time

| % Total Unknown Impurities | | | |
|---|---|---|---|
| Time point | Sample 1 | Sample 2 | Average |
| initial | 0.118 | 0.119 | 0.1185 |
| 1 week | 1.120 | 1.151 | 1.136 |
| 2 weeks | 3.379 | 3.625 | 3.502 |

Comparative Example 4

A composition not in accordance with the present invention was prepared by mixing equal amounts of quetiapine fumarate and maleic acid, i.e., 1:1 ratio. The composition was placed in an open container and subjected to accelerated stability conditions of 60° C. and 60% humidity for two weeks. The impurity profile of the composition was determined by HPLC as follows:

| % Unknown Impurity with RRT* 0.33 | | | |
|---|---|---|---|
| Time point | Sample 1 | Sample 2 | Average |
| initial | 0.0137 | 0.0136 | 0.0137 |
| 1 week | 0.1411 | 0.1536 | 0.1474 |
| 2 weeks | 0.3128 | 0.3628 | 0.3378 |

*RRT = relative retention time

| % Unknown Impurity with RRT* 0.36 | | | |
|---|---|---|---|
| Time point | Sample 1 | Sample 2 | Average |
| Initial | Below Detectable limits | Below Detectable limits | Below Detectable limits |
| 1 week | 0.5761 | 0.6746 | 0.6254 |
| 2 weeks | 1.2091 | 1.4720 | 1.3406 |

*RRT = relative retention time

| % Unknown Impurity with RRT* 0.41 | | | |
|---|---|---|---|
| Time point | Sample 1 | Sample 2 | Average |
| initial | Below Detectable limits | Below Detectable limits | Below Detectable limits |
| 1 week | Below Detectable limits | Below Detectable limits | Below Detectable limits |
| 2 weeks | 0.0633 | 0.0508 | 0.0571 |

*RRT = relative retention time

| % Unknown Impurity with RRT* 0.48~0.51 | | | |
|---|---|---|---|
| Time point | Sample 1 | Sample 2 | Average |
| initial | 0.0347 | 0.0332 | 0.0340 |
| 1 week | 0.3403 | 0.3977 | 0.3690 |
| 2 weeks | 0.8782 | 1.0318 | 0.9550 |

*RRT = relative retention time

| % Unknown Impurity with RRT* 0.55~0.59 | | | |
|---|---|---|---|
| Time point | Sample 1 | Sample 2 | Average |
| Initial | Below Detectable limits | Below Detectable limits | Below Detectable limits |
| 1 week | 68.9090 | 73.5815 | 71.2453 |
| 2 weeks | 76.6554 | 79.3466 | 78.001 |

*RRT = relative retention time

| % Unknown Impurity with RRT* 0.89 | | | |
|---|---|---|---|
| Time point | Sample 1 | Sample 2 | Average |
| initial | 0.0694 | 0.0700 | 0.0697 |
| 1 week | 0.0420 | 0.0363 | 0.0392 |
| 2 weeks | 0.0394 | 0.0343 | 0.0369 |

*RRT = relative retention time

| % Total Unknown Impurities | | | |
|---|---|---|---|
| Time point | Sample 1 | Sample 2 | Average |
| initial | 0.118 | 0.117 | 0.118 |
| 1 week | 70.008 | 74.844 | 72.426 |
| 2 weeks | 79.158 | 82.298 | 80.728 |

Comparative Example 5

A composition not in accordance with the present invention was prepared by mixing equal amounts of quetiapine fumarate and malic acid, i.e., 1:1 ratio. The composition was placed in an open container and subjected to accelerated stability conditions of 60° C. and 60% humidity for two weeks. The impurity profile of the composition was determined by HPLC as follows:

| % Unknown Impurity with RRT* 0.27~0.33 | | | |
|---|---|---|---|
| Time point | Sample 1 | Sample 2 | Average |
| initial | 0.0142 | 0.0147 | 0.0145 |
| 1 week | 0.762 | 0.832 | 0.797 |
| 2 weeks | 1.7530 | 1.5296 | 1.6413 |

*RRT = relative retention time

| % Unknown Impurity with RRT* 0.36 | | | |
|---|---|---|---|
| Time point | Sample 1 | Sample 2 | Average |
| Initial | Below Detectable limits | Below Detectable limits | Below Detectable limits |
| 1 week | 4.971 | 5.591 | 5.281 |
| 2 weeks | 9.6604 | 8.6327 | 9.1466 |

*RRT = relative retention time

| % Unknown Impurity with RRT* 0.48~0.50 | | | |
|---|---|---|---|
| Time point | Sample 1 | Sample 2 | Average |
| initial | 0.0335 | 0.0336 | 0.0336 |
| 1 week | 29.6478 | 34.3748 | 32.0113 |
| 2 weeks | 41.9445 | 38.6429 | 40.2937 |

*RRT = relative retention time

| % Unknown Impurity with RRT* 0.59 | | | |
|---|---|---|---|
| Time point | Sample 1 | Sample 2 | Average |
| Initial | | | |
| 1 week | 1.2120 | 1.4466 | 1.3293 |
| 2 weeks | 2.4228 | 2.3229 | 2.3729 |

*RRT = relative retention time

| % Unknown Impurity with RRT* 0.89 | | | |
|---|---|---|---|
| Time point | Sample 1 | Sample 2 | Average |
| initial | 0.0686 | 0.0696 | 0.0691 |
| 1 week | 0.0590 | 0.0556 | 0.0573 |
| 2 weeks | 0.0921 | 0.0930 | 0.0926 |

*RRT = relative retention time

| % Total Unknown Impurities | | | |
|---|---|---|---|
| Time point | Sample 1 | Sample 2 | Average |
| initial | 0.117 | 0.117 | 0.117 |
| 1 week | 36.652 | 42.299 | 39.476 |
| 2 weeks | 55.873 | 51.221 | 53.547 |

Comparative Example 6

A composition not in accordance with the present invention was prepared by mixing equal amounts of quetiapine fumarate and sodium hydrogen tartrate monohydrate, i.e., 1:1 ratio. The composition was placed in an open container and subjected to accelerated stability conditions of 60° C. and 60% humidity for two weeks. The impurity profile of the composition was determined by HPLC as follows:

| % Unknown Impurity with RRT* 0.47 | | | |
|---|---|---|---|
| Time point | Sample 1 | Sample 2 | Average |
| initial | 0.0357 | 0.0377 | 0.0367 |
| 1 week | 0.0363 | 0.0374 | 0.0369 |
| 2 weeks | 0.0352 | 0.0375 | 0.0364 |

*RRT = relative retention time

| % Unknown Impurity with RRT* 0.89 | | | |
|---|---|---|---|
| Time point | Sample 1 | Sample 2 | Average |
| initial | 0.0705 | 0.0696 | 0.0701 |
| 1 week | 0.0700 | 0.0713 | 0.0707 |
| 2 weeks | 0.0719 | 0.0729 | 0.0724 |

*RRT = relative retention time

| % Total Unknown Impurities | | | |
|---|---|---|---|
| Time point | Sample 1 | Sample 2 | Average |
| initial | 0.106 | 0.107 | 0.107 |
| 1 week | 0.106 | 0.109 | 0.108 |
| 2 weeks | 0.107 | 0.110 | 0.109 |

Example 3

A pharmaceutical composition and controlled release dosage form in accordance with the present invention was prepared as follows:

Approximately 75 grams of Lactitol NF was dissolved in approximately 145 grams of purified water to prepare a Lactitol solution.

Approximately 1151.3 grams of quetiapine hemifumarate that had been sieved through a 120 mesh sieve and approximately 810.0 grams of succinic acid that had been sieved through a 80 mesh sieve were mixed for about 5 minutes. The mixture was than sprayed with 200 ml of the Lactitol solution to create granules. The granules were dried and sized with granules smaller than 20 mesh being discarded.

Approximately 203.63 grams of the dried and sized granules were then blended with approximately 20.7 grams of LUBRITAB (hydrogenated vegetable oil), 2.3 grams of talc and 1.15 grams of colloidal silicon dioxide for about 15 minutes in a V type blender. Approximately 2.3 grams of magnesium stearate was added to the blend and further blended for about 5 minutes.

The blend was then compressed into controlled release quetiapine tablets using a rotary tablet press with an 8*16 mm capsule shaped die.

A placebo rate controlling layer was subsequently compressed onto one side of the controlled released quetiapine tablet using a rotary tablet press. The placebo rate controlling layer was prepared from granules obtained by mixing approximately 39.5 grams of lactose NF, 10 grams of LUBRITAB and 0.5 grams of talc in a V type blender.

A 200 mg controlled release quetiapine tablet in accordance with the present invention and without any materials that gel or swell were placed in an aqueous environment according to the above procedure with the following composition:

| Ingredient | % w/w | Mg/tablet |
| --- | --- | --- |
| Quetiapine Hemifumarate | 41.09 | 230.26 |
| Succinic Acid | 28.93 | 162.11 |
| Lactitol | 2.68 | 15.01 |
| LUBRITAB | 7.39 | 41.43 |
| Colloidal Silicon Dioxide | 0.41 | 2.31 |
| Magnesium Stearate | 0.82 | 4.61 |
| Talc | 0.82 | 4.61 |
| Active Tablet Subtotal | 82.15 | 460.33 |
| Lactose | 14.10 | 79.0 |
| LUBRITAB | 3.57 | 20.0 |
| Talc | 0.18 | 1.0 |
| Placebo Layer Subtotal | 17.85 | 100.0 |
| Total | 100.0 | 560.33 |

Three (3) of the 200 mg controlled release dosage forms prepared in Example 3 were tested according to the procedures described in United States Pharmacopeia 29 using a Type I (basket) apparatus at 37° C., 100 rpms and 900 ml of 0.1N HCl. The release profile determined by the testing was:

| Time | % Released |
| --- | --- |
| 2 hours | 44.7 |
| 4 hours | 61.1 |
| 6 hours | 73.0 |
| 8 hours | 82.1 |
| 12 hours | 94.2 |
| 18 hours | 98.7 |
| 24 hours | 100.4 |

The pH of the tablet prepared in Example 3 was measured by preparing a 1% weight by volume aqueous suspension and a 5% weight by volume aqueous suspension of the tablet ingredients at 25° C. The tablet ingredients were in a powder form, i.e not tableted, and suspended in purified water. The pH was measured using a commercially available pH probe and determined to be 3.68 for the 1% suspension and 3.46 for the 5% suspension.

Example 4

A pharmaceutical composition and controlled release dosage form in accordance with the present invention was prepared according to the procedure described in Example 3 with the following composition:

| Ingredient | % w/w | Mg/tablet |
| --- | --- | --- |
| Quetiapine Hemifumarate | 41.3 | 230.26 |
| Succinic Acid | 29.0 | 162 |
| Lactitol | 2.7 | 15 |
| LUBRITAB | 7.4 | 41.4 |
| Magnesium Stearate | 0.8 | 4.6 |
| Talc | 0.8 | 4.6 |
| Active Tablet Subtotal | 82.1 | 457.86 |
| Lactose | 14.2 | 79.0 |
| LUBRITAB | 3.6 | 20.0 |
| Talc | 0.2 | 1.0 |
| Placebo Layer Subtotal | 17.9 | 100.0 |
| Total | 100.0 | 557.9 |

Three (3) of the 200 mg controlled release dosage forms prepared in Example 4 were tested according to the procedures described in United States Pharmacopeia 29 using a Type I (basket) apparatus at 37° C., 100 rpms and 900 ml of 0.1N HCl. The release profile determined by the testing was:

| Time | % Released |
| --- | --- |
| 2 hours | 43.6 |
| 4 hours | 59.3 |
| 6 hours | 71.1 |
| 8 hours | 80.5 |
| 12 hours | 92.0 |
| 18 hours | 96.6 |
| 24 hours | 98.4 |

Examples 5-7

Pharmaceutical compositions and controlled release dosage forms in accordance with the present invention were prepared according to the procedure described in Example 3 with the following composition:

| Ingredient | Mg/tablet (Ex 5) | Mg/tablet (Ex 6) | Mg/tablet (Ex 7) |
| --- | --- | --- | --- |
| Quetiapine Hemifumarate | 57.56 | 345.38 | 460.51 |
| Succinic Acid | 38.38 | 243.17 | 307.06 |
| Lactitol | 3.75 | 22.52 | 30.01 |
| LUBRITAB | 24.11 | 60.00 | 55.41 |
| Colloidal Silicon Dioxide | 0.64 | 3.50 | 4.37 |
| Magnesium Stearate | 1.27 | 6.90 | 8.75 |
| Talc | 1.27 | 6.90 | 8.75 |
| Active Tablet Subtotal | 126.98 | 688.36 | 874.86 |
| Lactose | 28.44 | 79.00 | 94.80 |
| LUBRITAB | 7.20 | 20.0 | 24.0 |
| Talc | 0.36 | 1.0 | 1.20 |
| Placebo Layer Subtotal | 36.00 | 100.0 | 120.0 |
| Total | 162.98 | 788.36 | 994.86 |

The pH of the tablets prepared in Examples 6 and 7 were determined according to the procedure described in Example 3. The pH of the 1% suspension of Example 6 was 3.65 and the pH of the 5% suspension of Example 6 was 3.46. The pH of the 1% suspension of Example 7 was 3.67 and the pH of the 5% suspension of Example 7 was 3.5.

Examples 8-9

Pharmaceutical compositions and immediate release dosage forms in accordance with the present invention were prepared according to the procedure described in Example 3 with the following composition:

| Ingredient | Mg/Tablet (Ex 8) | Mg/tablet (Ex 9) |
|---|---|---|
| Quetiapine Hemifumarate | 230.26 | 230.26 |
| Succinic Acid | 162 | 162 |
| Lactitol | 15 | 15 |
| Colloidal silicon dioxide | 2.3 | — |
| Magnesium Stearate | 4.6 | 4.6 |
| Talc | 4.6 | 4.6 |
| Active Tablet Subtotal | 418.76 | 416.46 |
| Lactose | 79.2 | 79.2 |
| Talc | 0.8 | 0.8 |
| Placebo Layer Subtotal | 80 | 80 |
| Total | 498.8 | 496.5 |

Three (3) of the 200 mg controlled release dosage forms prepared in Examples 8 and 9 were tested according to the procedures described in United States Pharmacopeia 29 using a Type I (basket) apparatus at 37° C., 100 rpms and 900 ml of 0.1N HCl. The release profile determined by the testing was:

| Time | Ex 8 % Released | Ex 9 % Released |
|---|---|---|
| 0.75 hours | 99.0 | 95.6 |
| 1 hours | 99.1 | 95.5 |

Example 10 (Prophetic)

A pharmaceutical composition and immediate release dosage form in accordance with the present invention can be prepared according to the procedure described in Example 3 with the following composition:

| Ingredient | Mg/Tablet (Ex 8) | Mg/tablet (Ex 9) |
|---|---|---|
| Quetiapine Hemifumarate | 230.26 | 230.26 |
| Fumaric Acid | 162 | 162 |
| Lactitol | 15 | 15 |
| Colloidal silicon dioxide | 2.3 | — |
| Magnesium Stearate | 4.6 | 4.6 |
| Talc | 4.6 | 4.6 |
| Active Tablet Subtotal | 418.76 | 416.46 |
| Lactose | 79.2 | 79.2 |
| Talc | 0.8 | 0.8 |
| Placebo Layer Subtotal | 80 | 80 |
| Total | 498.8 | 496.5 |

Examples 11-13 (Prophetic)

Pharmaceutical compositions and controlled release dosage forms in accordance with the present invention can be prepared according to the procedure described in Example 3 with the following composition:

| Ingredient | Mg/tablet (Ex 11) | Mg/tablet (Ex 12) | Mg/tablet (Ex 13) |
|---|---|---|---|
| Quetiapine Hemifumarate | 230.26 | 345.38 | 460.51 |
| Fumaric Acid | 162.11 | 243.17 | 307.06 |
| Lactitol | 15.01 | 22.52 | 30.01 |
| LUBRITAB | 41.43 | 60.00 | 55.41 |
| Colloidal Silicon Dioxide | 2.31 | 3.50 | 4.37 |
| Magnesium Stearate | 4.61 | 6.90 | 8.75 |
| Talc | 4.61 | 6.90 | 8.75 |
| Active Tablet Subtotal | 460.33 | 688.36 | 874.86 |
| Lactose | 79.0 | 79.00 | 94.80 |
| LUBRITAB | 20.0 | 20.0 | 24.0 |
| Talc | 1.0 | 1.0 | 1.20 |
| Placebo Layer Subtotal | 100.00 | 100.0 | 120.0 |
| Total | 560.33 | 788.36 | 994.86 |

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

The invention claimed is:

1. A pharmaceutical composition comprising a mixture of: (i) a drug selected from the group consisting of quetiapine fumarate or quetiapine hydrochloride (ii) an organic acid selected from the group consisting of succinic acid or a mixture of succinic and fumaric acid; and (iii) at least one pharmaceutically acceptable excipient wherein the pH of a 1% weight by volume solution or suspension of the composition in purified water is less than 5 and the ratio of quetiapine fumarate or quetiapine hydrochloride to the organic acid is about 1:3 to about 3:1.

2. The composition as defined in claim 1 wherein the drug is quetiapine fumarate.

3. The composition as defined in claim 1 wherein the pH is less than 4.

4. The composition as defined in claim 1 wherein the organic acid is succinic acid.

5. The composition as defined in claim 1 wherein the composition is a mixture of succinic acid and fumaric acid.

6. The composition as defined in claim 1 wherein the composition is a solid oral dosage form.

7. The composition as defined in claim 6 wherein the composition is a solid oral controlled release dosage form.

8. The composition as defined in claim 7 wherein the solid oral controlled release dosage form is a hydrophobic matrix that is free of any material that gels or swells.

9. An oral solid controlled release dosage form comprising a mixture of:
   a. quetiapine fumarate or quetiapine hydrochloride;
   b. an organic acid selected from the group consisting of succinic acid or a mixture of succinic acid and fumaric acid; and
   c. a rate controlling excipient, wherein the pH of a 1% weight by volume solution or suspension of the dosage form in purified water is less than 5 and the ratio of quetiapine fumarate or quetiapine hydrochloride to the organic acid is about 1:3 to about 3:1.

10. The solid controlled release dosage form as defined in claim 9 wherein the dosage form is a matrix tablet.

11. The solid controlled release dosage form as defined in claim 10 wherein the rate controlling excipient is a hydrophobic material.

12. The solid controlled release dosage form as defined in claim 10 wherein the rate controlling excipient is a hydrophilic material.

13. The solid controlled release dosage form as defined in claim 9 wherein the drug is quetiapine fumarate.

14. The solid controlled release dosage form as defined in claim 9 wherein pH is less than 4.

15. The solid controlled release dosage form as defined in claim 10 wherein matrix is free of any material that gels or swells.

16. The solid controlled release dosage form as defined in claim 9 wherein the organic acid is succinic acid.

17. The solid controlled release dosage form as defined in claim 9 wherein the organic acid is a mixture of succinic and fumaric acid.

18. A pharmaceutical composition comprising a mixture of: (i) quetiapine fumarate (ii) succinic acid and (iii) at least one pharmaceutically acceptable excipient wherein the pH of a 1% weight by volume solution or suspension of the composition in purified water is less than 4 and the ratio of quetiapine fumarate to the succinic acid is about 1:3 to about 3:1.

19. The pharmaceutical composition as defined in claim 18 wherein the composition is a solid oral controlled release dosage form.

20. The pharmaceutical composition as defined in claim 18 wherein pharmaceutically acceptable excipient is a rate controlling excipient.

* * * * *